United States Patent [19]

Sekiguchi et al.

[11] 4,318,823

[45] Mar. 9, 1982

[54] LIGHT COLORED HOMOGENEOUS AND AQUEOUS ALPHA OLEFIN SULFONATE SOLUTIONS

[75] Inventors: Shizuo Sekiguchi, Funabashi; Tetsuo Tano; Kyozo Kitano, both of Chiba; Toshiaki Ogoshi, Funabashi, all of Japan

[73] Assignee: The Lion Fat & Oil Co., Ltd., Tokyo, Japan

[21] Appl. No.: 102,595

[22] Filed: Dec. 12, 1979

[30] Foreign Application Priority Data

Dec. 15, 1978 [JP] Japan ................................. 53-154244

[51] Int. Cl.$^3$ ........................ B01F 17/02; C11D 1/12; C07C 139/00
[52] U.S. Cl. ................................... 252/353; 252/555; 260/504 R; 260/513 T
[58] Field of Search ............ 260/513 T, 504 R, 504 S; 252/555, 353

[56] References Cited

U.S. PATENT DOCUMENTS 3,531,518 9/1970 Ohren et al. .................... 260/513 T
3,919,300 11/1975 Nagayama et al. ............. 260/513 T

OTHER PUBLICATIONS

Gilbert, "Sulfonation and Related Reactions", (1965) pp. 42–46.

*Primary Examiner*—Alan Siegel
*Attorney, Agent, or Firm*—Blanchard, Flynn, Thiel, Boutell & Tanis

[57] ABSTRACT

Light colored homogeneous and aqueous alpha olefin sulfonate solutions wherein about 10 to about 30 wt. % of the sulfonate contained in said alpha olefin sulfonate solutions is 4-hydroxyalkane sulfonate.

3 Claims, No Drawings

LIGHT COLORED HOMOGENEOUS AND AQUEOUS ALPHA OLEFIN SULFONATE SOLUTIONS

BACKGROUND OF THE INVENTION

The present invention relates to light colored homogeneous and aqueous alpha olefin sulfonate solutions. More particularly, it relates to light colored aqueous alpha olefin sulfonate solutions which are free from the occurrence of turbidity therein even when they are allowed to stand for a long period of time.

In general, aqueous alpha olefin sulfonate solutions (which will be referred to as "AOS solutions" for short hereinafter) are manufactured by sulfonating alpha olefins with sulfur trioxide/inert diluent mixture, neutralizing the resulting sulfonated products with alkali solutions such as an aqueous sodium hydroxide solution, and further hydrolyzing the same in the presence of alkali. However, since the reaction between alpha olefins and sulfur trioxide is rapid in nature, it is customary for the AOS solutions obtained according to the above-mentioned method to be colored considerably. Despite this, light colored AOS solutions can be obtained by either employing relatively mild reaction conditions for the sulfonation or subjecting the colored AOS solutions to a bleaching treatment. Employment of the method disclosed, for instance, in Japanese Patent Publication No. 48409/1974 permits the production of light colored AOS solutions without an additional bleaching treatment.

However, it is to be noted that the light colored AOS solutions prepared under mild sulfonation conditions are superior in respect of their quality as surface active agents in comparison with the AOS solutions prepared using a bleaching treatment, but on the other hand they are defective in that turbidity occurs during storage and in an extreme instance the solutions are divided into two phases. The occurrence of turbidity or phase separation as mentioned above inevitably not only proves an obstacle to the storage and handling of the AOS solutions but also deteriorates the commercial value of the AOS solutions per se. Therefore, it is inevitably necessary to prevent the occurrence of such phenomena as mentioned above.

SUMMARY OF THE INVENTION

We have carried out a series of investigations, hitherto overlooked, on the occurrence of turbidity and phase separation in the AOS solutions and found that turbidity first takes place in the solution and successively increases, whereby the solution is divided into two phases, namely, a transparent upper phase and an opaque or semitransparent lower phase, and that a difference in composition can scarcely be observed between the upper and lower phases but a laminar micelle structure or liquid crystal structure is formed on the lower phase side.

In more detail, we have found that AOS dissolves to form an aqueous solution with micelle formation, but as the concentration and temperature of said solution increase, micelles associate with each other to thereby form large micelles gradually, being accompanied with the conversion of laminar micelles into liquid crystals, and finally different phases are formed in the solution and that this phenomenon takes place also when the AOS solutions are left standing for a long period of time. Thus, we have discovered that the appearance of laminar micelles or liquid crystals is closely related with the amount of hydroxyalkane sulfonate contained in AOS, particularly that of 4-hydroxyalkane sulfonate, and the formation of laminar micelles or liquid crystals can be prevented by maintaining the amount of 4-hydroxyalkane sulfonate in the range of 10% by weight or more, preferably in the range of from 10% to 30% by weight based on the total amount of sulfonate, and therefore the occurrence of turbidity in the AOS solutions or phase separation can be prevented substantially.

As previously stated, AOS solutions are manufactured by sulfonating alpha olefins with diluted sulfur trioxide, neutralizing the resulting sulfonated products with alkali solutions, and then hydrolyzing the same. In order to obtain light colored AOS solutions intended to be serviceable as surface active agents, alpha olefin having 10 to 20 carbon atoms is used as a starting olefin, and there are conventionally employed a sulfonation method which comprises flowing the starting olefin downwards in the form of a thin-film state, and contacting the thin-film olefin with sulfur trioxide, diluted with inert gas to have a concentration ranging from 2% to 20% by volume, under the conditions including the molar ratio of sulfur trioxide to olefin of from about 1.0 to about 1.2 and the temperature of from 40° C. to 70° C. The thus obtained sulfonation product of alpha olefin is successively neutralized with an aqueous solution of one alkali selected from the group consisting of alkali metal hydroxides and alkaline earth metal hydroxides and oxides, and further hydrolyzing the same at elevated temperature, whereby a light colored AOS solution is obtained. This solution consists essentially of alkene sulfonate and hydroxyalkane sulfonate and contains, as small amounts of ingredients, disulfonate and others, wherein the amount of 4-hydroxyalkane sulfonate is less than 10% by weight based on the total amount of sulfonate.

And, in order that the amount of 4-hydroxyalkane sulfonate may be in excess of 10% by weight based on the total amount of sulfonate, there is employed a method which comprises ageing the sulfonation product of alpha olefin thoroughly prior to neutralization thereof for the purpose of increasing the amount of 1,4-sultone (intra-molecular ester of 4-hydroxyalkane sulfonate) contained in the sulfonation product or adding separately prepared 4-hydroxyalkane sulfonate to the sulfonation product.

PREPARATION OF LIGHT COLORED HOMOGENEOUS ALPHA OLEFIN SULFONATE SOLUTIONS

Although there are some variations depending on the conditions for hydrolysis, it may generally be said that about 50% of the 1,4-sultone contained in the sulfonation product is hydrolyzed to alkene sulfonate and the remaining about 50% thereof is only hydrolyzed to 4-hydroxyalkane sulfonate. Accordingly, when ageing of the sulfonation product is effected with the intention of increasing the amount of 1,4-sultone contained therein, it is necessary for the amount of said 1,4-sultone to be increased to at least 20 wt. % or more. And, it is desirable for that purpose that the sulfonation product, maintained at a temperature ranging from about 50° C. to about 60° C., be subjected to ageing for about 15 minutes to about 30 minutes, preferably for about 20 minutes with stirring. When ageing is effected at a low temperature it takes a long period of time, the resulting product is colored very remarkably, while when ageing is effected at a high temperature the product is colored rapidly. Due to this, it is necessary to select an optimum temperature for ageing. If this condition is met, some lowering of the product's color tone may be tolerated for practical purposes.

When a method is employed which comprises addition of 4-hydroxyalkane sulfonate, said 4-hydroxyalkane sulfonate may be as usual prepared through the steps of sulfonating alpha olefin, ageing the resulting sulfonation product at elevated temperature for isomerization of 1,2-sultone and 1,3-sultone into 1,4-sultone, then neutralizing this sulfonation product with an alkali solution and further subjecting the same to hydrolysis. The 4-hydroxyalkane sulfonate obtained herein assumes the form of an aqueous solution. This aqueous solution per se can be added to the AOS solution. And, as revealed in the under-mentioned Examples, it is also possible to isolate 4-hydroxyalkane sulfonate and adding this to the AOS solution. In any case, the addition of 4-hydroxyalkane sulfonate is more desirable in respect of obtaining a light colored AOS solution than that of increasing the amount of 1,4-sultone by ageing the sulfonation product.

In the AOS solutions according to the present invention, in which the ratio of 4-hydroxyalkane sulfonate to the total sulfonate is 10% by weight or more, even when their concentrations are 25% by weight or more, typically in the range of from 30% to 50% by weight, there is no possibility that turbidity or phase separation is caused even when they are liable to temperature variations or stored for a long period of time. Therefore, the light colored homogeneous AOS solutions according to the present invention, owing to their superior storage stability, should safely be said capable of giving promise of handling ease and increasing the quality as surface active agents.

EXAMPLE I

A sulfonation product X was obtained by subjecting $C_{14}$-$C_{16}$ alpha olefin ($C_{14}$/$C_{16}$=60/40, MW=205) to sulfonation under the conditions: reaction temperature 50° C., molar ratio of $SO_3$ to olefin 1.07, $SO_3$ supplying rate 1.56 g/minute and $SO_3$ gas concentration 1.5% by volume, in a laboratory glass-made film type reactor (inner diameter 6 mm$\phi$, length 1.2 m). Next, this sulfonation product X was neutralized with a NaOH solution, and then the same was placed in a 1 l autoclave and subjected to hydrolysis with stirring for 20 minutes, thereby obtaining an AOS solution Y wherein the total amount of sulfonate is 39% by weight, and the amount of 4-hydroxyalkane sulfonate is 4.5% by weight (based on the total amount of sulfonate).

This AOS solution Y was measured to determine the rate of reaction by means of the petroleum ether extraction method and to determine the color tone of the solution Y having a concentration of 5% by weight by means of spectrophotometry, respectively. The obtained results were as shown below.

Rate of reaction, 96.6%; Color tone, 32.

Color tone measurement was effected using a spectrophotometer manufactured by HITACHI LTD. and the color tone was expressed in terms of the value ($-\log T\times 1000$) obtained under the condition of employing a wavelength of 420 mm, slit width of 0.05 mm and a 1 cm glass cell.

Next, the above-mentioned AOS solution Y was placed in a broad-mouth bottle made of glass and was left standing at a temperature of about 30° C. for a week. The external appearance observation of this AOS solution showed the occurrence of turbidity therein.

EXAMPLE II

[Preparation and isolation of 4-hydroxyalkane sulfonate]

An alpha olefin sulfonation product was obtained according to the same procedure as employed in Example I except that the molar ratio of $SO_3$ to olefin was changed from 1.07 to 1.1. This sulfonation product was heated to a temperature ranging from 95° C. to 100° C. with stirring so that 1,2-sultone and 1,3-sultone contained in the sulfonation product were isomerized to form 1,4-sultone. This sulfonation product was successively neutralized with a 5%-NaOH solution. Thereafter, ethanol was added thereto so as to obtain a 50% EtOH solution, and 1,4-sultone was extracted therefrom using n-pentane. Next, the n-pentane was distilled out to recover the 1,4-sultone. Anhydrous toluene and anhydrous NaOH were added thereto and the resulting mixture was subjected to hydrolysis at a temperature ranging from 110° C. to 120° C. for 1 to 2 hours in an autoclave.

After completion of said hydrolysis, the toluene was distilled out under reduced pressure, and the obtained residue was dissolved in a 95% EtOH solution and centrifugally separated, thereby removing inorganic substances (mainly sodium sulfate). Next, water was added thereto to obtain a 50% EtOH solution, thereafter the unreacted sultone and remaining toluene were removed therefrom by extraction using petroleum ether, and then the same, after the water and ethanol had been distilled out of the 50% EtOH layer under reduced pressure, was dried for about 10 hours by means of a vacuum drier, whereby there were obtained light yellow crystals of sodium 4-hydroxyalkane sulfonate.

Next, the hydroxyalkane sulfonate crystals were added to the AOS solution Y prepared by the same procedure as employed in Example I, whereby there were prepared AOS solutions, A, B, C, D, E and F wherein the ratios of 4-hydroxyalkane sulfonate to the total sulfonate are 7%, 10%, 12%, 15%, 25% and 30% by weight respectively and the concentration of the total sulfonates of each solution is 39% by weight. Thereafter, each solution, in the same way as Example I, was placed in a broad-mouth bottle and left standing at a temperature of about 30° C. for 1 week. No substantial change was observed in respect of color tone between the respective AOS solutions, but the occurrence of turbidity was observed only with reference to AOS solution A in which the ratio of 4-hydroxyalkane sulfonate to the total sulfonate is 7% by weight.

EXAMPLE III

The same procedure as described in the aforesaid Example I was repeated to prepare sulfonation product X. Thereafter, this sulfonation product was heated to 40° C., and was subjected to ageing with stirring for 2 hours. Next, the sulfonation product after ageing was neutralized and hydrolyzed under the same conditions as defined in Example I to thereby obtain AOS solution G wherein the amount of the total sulfonate is 39% by weight and that of the 4-hydroxyalkane sulfonate is 13.6% by weight (based on the total sulfonate).

This solution G was placed in a broad-mouth bottle and was left standing at a temperature of about 30° C. for 1 week, whereby the occurrence of turbidity could not be observed therein.

In the case of this example, furthermore, the rate of reaction and the color tone of AOS solution were measured to be 96.9% and 45 respectively in accordance with the same measuring procedure as employed in Example I.

What is claimed is:

1. A process for preparing a light colored, homogeneous, aqueous, alpha-olefin sulfonate solution which does not develop turbidity when it is allowed to stand for a long period of time, which comprises the steps of: preparing an aqueous $C_{10}$–$C_{20}$ alpha-olefin sulfonate solution containing less than 10% by weight of 4-hydroxyalkane sulfonate, based on the total weight of sulfonates in said solution; then adding to and dissolving in said solution an additional quantity of separately prepared 4-hydroxyalkane sulfonate derived from $C_{10}$–$C_{20}$ alpha-olefin to increase the concentration of 4-hydroxyalkane sulfonate in said solution to a value in the range of from 10 to 30% by weight, based on the total weight of sulfonates in said solution.

2. A process according to claim 1 in which said separately prepared 4-hydroxyalkane sulfonate has been prepared by sulfonating $C_{10}$–$C_{20}$ alpha-olefin with a sulfur trioxide/inert gas mixture to obtain a sulfonation product containing 1,2-sultone and 1,3-sultone, then heating said sulfonation product with stirring to a temperature in the range of from about 95° to about 100° C. to isomerize the 1,2-sultone and 1,3-sultone and transform same into 1,4-sultone, then neutralizing said sulfonation product with an aqueous alkali solution to obtain a neutralized sulfonation product, then mixing said neutralized sulfonation product with ethanol to obtain an ethanol solution of said neutralized sulfonation product, then extracting the 1,4-sultone from said ethanol solution with toluene to obtain an extract of 1,4-sultone in toluene, then distilling off toluene from said extract to recover the 1,4-sultone, then hydrolyzing the thus-recovered 1,4-sultone by mixing same with anhydrous NaOH and anhydrous toluene to obtain a hydrolysis product containing sodium 4-hydroxyalkane sulfonate, then recovering the sodium 4-hydroxyalkane sulfonate from said hydrolysis product and then drying it to obtain sodium 4-hydroxyalkane sulfonate crystals.

3. A process for preparing a light colored, homogeneous, alpha-olefin sulfonate solution which does not develop turbidity when it is allowed to stand for a long period of time, which comprises the steps of: sulfonating $C_{10}$–$C_{20}$ alpha-olefin by flowing said alpha-olefin in the form of a thin film and contacting said thin film of alpha-olefin with sulfur trioxide/inert gas mixture containing from 2 to 20% by volume of sulfur trioxide, wherein the molar ratio of said sulfur trioxide to said alpha-olefin is from about 1.0 to about 1.2, at a temperature of from 40° C. to 70° C., to obtain a sulfonation reaction product, then neutralizing the sulfonation reaction product with an aqueous alkali solution and then hydrolyzing the neutralized sulfonation reaction product to obtain a light colored alpha-olefin sulfonate solution containing less than 10% by weight of 4-hydroxyalkane sulfonate, based on the total weight of sulfonates in said light colored alpha-olefin sulfonate solution;

separately preparing 4-hydroxyalkane sulfonate by sulfonating $C_{10}$–$C_{20}$ alpha-olefin with a sulfur trioxide/inert gas mixture to obtain a sulfonation product containing 1,2-sultone and 1,3-sultone, then heating said sulfonation product with stirring to a temperature in the range of from about 95° to about 100° C. to isomerize the 1,2-sultone and 1,3-sultone and transform same into 1,4-sultone, then neutralizing said sulfonation product with an aqueous alkali solution to obtain a neutralized sulfonation product, then extracting and recovering the 1,4-sultone from said neutralized sulfonation product, then hydrolyzing the thus-recovered 1,4-sultone with anhydrous NaOH to obtain a hydrolysis product containing sodium 4-hydroxyalkane sulfonate, then recovering the sodium 4-hydroxyalkane sulfonate from said hydrolysis product;

and then adding to and dissolving in said light colored alpha-olefin sulfonate solution an additional quantity of said sodium 4-hydroxyalkane sulfonate to increase the concentration of 4-hydroxyalkane sulfonate in said light colored alpha-olefin sulfonate solution to a value in the range of from 10 to 30% by weight, based on the total weight of sulfonates in said light colored alpha-olefin sulfonate solution.

* * * * *

UNITED STATES PATENT AND TRADEMARK OFFICE
CERTIFICATE OF CORRECTION

PATENT NO. : 4 318 823
DATED : March 9, 1982
INVENTOR(S) : Shizuo Sekiguchi et al It is certified that error appears in the above—identified patent and that said Letters Patent is hereby corrected as shown below:

ON THE TITLE PAGE,

Change the Assignee's name from "The Lion Fat & Oil Co., Ltd." to ---Lion Corporation---.

Signed and Sealed this

Seventh Day of December 1982

[SEAL]

Attest:

Attesting Officer

GERALD J. MOSSINGHOFF
Commissioner of Patents and Trademarks